(12) United States Patent
Martel (10) Patent No.: US 6,459,448 B1
(45) Date of Patent: Oct. 1, 2002

(54) SYSTEM AND METHOD FOR AUTOMATICALLY INSPECTING ARRAYS OF GEOMETRIC TARGETS

(75) Inventor: Thomas Joseph Martel, Dewitt, NY (US)

(73) Assignee: K-G Devices Corporation, Dewitt, NY (US)

( * ) Notice: Subject to any disclaimer, the term of this patent is extended or adjusted under 35 U.S.C. 154(b) by 0 days.

(21) Appl. No.: 09/552,685

(22) Filed: Apr. 19, 2000

(51) Int. Cl.[7] .................................................. H04N 7/18
(52) U.S. Cl. ......................................... 348/125; 348/92
(58) Field of Search ...................... 348/86–92, 125–130, 348/180; 382/141–152; 356/429–431, 237.1–237.6, 238.1–238.3, 239.1–239.8, 240.1; 702/35; 364/468.17

(56) References Cited

U.S. PATENT DOCUMENTS

| | | | |
|---|---|---|---|
| 3,988,530 A | 10/1976 | Ikegami et al. ................. 178/6 |
| 4,349,880 A | * 9/1982 | Southgate et al. ............. 702/40 |
| 4,403,294 A | 9/1983 | Hamada et la. .............. 364/507 |
| 4,486,777 A | 12/1984 | Yamamura et al. .......... 358/106 |
| 4,519,041 A | 5/1985 | Fant et al. .................... 364/552 |
| 4,707,734 A | 11/1987 | Labinger et al. ............. 358/106 |
| 4,771,468 A | 9/1988 | Batchelder et al. ............. 382/8 |
| 4,797,939 A | 1/1989 | Hoki et al. ..................... 382/8 |
| 4,799,175 A | * 1/1989 | Sano et al. ................... 364/552 |
| 5,048,094 A | 9/1991 | Aoyama et al. ................ 382/8 |
| 5,111,411 A | 5/1992 | Browne ....................... 364/559 |
| 5,268,968 A | 12/1993 | Yoshida ......................... 382/8 |
| 5,513,275 A | 4/1996 | Khalaj et al. ................ 382/149 |
| 5,544,256 A | 8/1996 | Brecher et al. .............. 382/149 |
| 5,659,630 A | * 8/1997 | Forslund ..................... 382/149 |
| 5,691,543 A | 11/1997 | Ishizaka ................. 250/559.06 |
| 5,815,198 A | 9/1998 | Vachtsevanos et al. ....... 348/88 |
| 5,926,268 A | 7/1999 | Bonewitz et al. ............ 356/240 |
| 5,926,556 A | 7/1999 | Douglas et al. ............. 382/142 |

FOREIGN PATENT DOCUMENTS

| | | | |
|---|---|---|---|
| JP | 4-265847 | 9/1992 | .......... G01N/21/88 |
| JP | 7-72097 | 3/1995 | .......... G01N/21/88 |
| JP | 9-159622 | 6/1997 | .......... G01N/21/89 |
| JP | 1-1295230 A2 | 10/1999 | .......... G01N/21/88 |

* cited by examiner

*Primary Examiner*—Vu Le
(74) *Attorney, Agent, or Firm*—Morgan, Lewis & Bockius LLP (57) ABSTRACT

A system and method for using electronically acquired imagery from a one-dimensional camera, to inspect an object for tolerance, color, blemishes, cracks or a wide variety of manufacturing defects that might be present in an object. The method used to detect manufacturing defects includes an algorithm for analyzing the pattern of annular elements in an array and detecting deviations from numerical acceptance norms, such as diameter, spacing, and symmetry, for the annular elements. In the inventive system, a one-dimensional video camera captures a single one-dimensional "slice" of target shape of an object with every line it scans. Each slice is broken down into "segments" consisting of sets of adjacent pixels that are similar in brightness, hue, or both. The one-dimensional camera delivers the segments to the system where they are sequenced. The system identifies every segment to determine what feature of the target shape the segment represents. Thereafter, predefined rules are used to determine if each identified segment deviates from numerical acceptance norms. The inventive method is thus used to analyze periodic arrays of any arbitrary target shape, thereby working in a range of different object acceptance norms and being easily adaptable to change from one set of norms to another.

47 Claims, 4 Drawing Sheets

IMAGE WITH SCAN LINE

FIG. 1-A

ROW SCANNED, SHOWN IN ISOLATION

FIG. 1-B

ROW SCANNED, POSITIONS ADJUSTED (SEE TEXT)

FIG. 1-C

RESULTING COMPOSITE IMAGE

SYSTEM AND METHOD FOR AUTOMATICALLY INSPECTING ARRAYS OF GEOMETRIC TARGETS

FIELD OF THE INVENTION

This invention relates to a computer system for inspecting objects for manufacturing defects and more particularly to an algorithm in the computer system for inspecting electronically acquired imagery of an object for a wide variety of manufacturing defects that might be present in the object.

BACKGROUND OF THE INVENTION

While advances in computer processing power have made processing of large amounts of data possible, an automated optical inspection problem for arrays of geometric targets still exists. Automated optical inspection is the inspection of electronically acquired imagery of an object for tolerance, color, blemishes, cracks or a wide variety of manufacturing defects that might be present in the object. The automated optical inspection problem arises, among other places, in the inspection of aperture masks used in CRT-type color monitors and television sets. Problems encountered during aperture masks inspections also occur during inspections of other objects, which include inspection of an array of annular targets with periodic data. Thus, two seemly different objects, such as flat panel displays and filters for filtering bacterial particles out of a product stream of bio-engineered vaccines and chemicals have the same inspection problem. Therefore, while the following discusses inspection of aperture masks with arrays of annular targets, it should be apparent to one of ordinary skill in the art that the invention relates to inspection of all objects with arrays of geometric targets.

Aperture masks generally are comprised of thin metal sheets perforated by hundreds of thousands of tiny holes. These holes are too small to see with an unaided eye and each hole has a precise shape, or profile. The shape of each hole varies slightly and definitely according to its position across the width and/or height of the mask. The degree to which the shape of these holes can be maintained in manufacturing of the aperture mask has a direct bearing on whether the mask can be used by a manufacturer.

Inspection of aperture masks during manufacturing is a particularly demanding problem because there are vast numbers of holes, at least several hundred thousand holes, in each mask. Aperture masks are relatively inexpensive to manufacture. Nonetheless, the shape of a single hole that is out of tolerance eventually shows up as a blemish that an end user can see in a finished product. For example, the end user will see a blemish in an image that is produced by a CRT-type color monitor, which includes the defective aperture mask. Thus, automated or manual inspection of each mask has to be performed. Automated inspection by a computer leads to a formidable data reduction problem since each hole has many pixels, thereby producing billions of pixels across the length and width of each mask.

Some manufacturers use human inspectors to manually inspect each mask but do not use any special magnification method. The human inspectors hold each mask up to the light and bend it in various ways to detect an irregular hole or area in the mask. While the manufacturing of the aperture masks is automated, inspections of the masks are performed by groups of inspectors. Each person in a group may inspect a particular section of the masks and inspections of the masks are performed at much slower rates than the rates at which they are manufactured. The manual inspection process also is a relatively expensive undertaking for the manufacturer.

A current automated method uses two-dimensional video cameras to analyze data on a computer. Thereafter various mathematical operations, such as edge detection, a gradient calculation, or some other type of transform to manipulate the data, are performed on the two-dimensional representation of the data. The automated method measures the inside and outside diameter of each hole to calculate whether the inner diameter is the right range of tolerance. This method generates an unusable and impractical amount of data that may only be analyzed by a very specialized and expensive computer. Moreover, by the time images large enough to analyze by video cameras are created, a microscopic processor is usually created for each hole. In an industrial environment, where there is a lot of vibration in the manufacturing process, masks that come out of the last stage of the manufacturing process vibrate slightly. This vibration is enough to make an image useless unless the image is taken over an extremely short time period.

What is needed, therefore, is an automated method for inspecting electronically acquired imagery of an object for a wide variety of manufacturing defects that might be present in the object. The method must be unaffected by the visual effects of mechanical vibration on an image while tolerating the effects of imperfect positioning of the target object by an operator or as a result of equipment shortcomings. The method also must work in a range of different object acceptance norms and must be easily adaptable to change from one set of norms to another. Moreover, the method must be expressible as a custom or semi-custom integrated circuit chip and it must scale well to a highly parallel implementation.

SUMMARY OF THE INVENTION

The present invention relates to a system and method for inspecting electronically acquired imagery, from a one-dimensional camera, of an object for tolerance, color, blemishes, cracks or a wide variety of manufacturing defects that might be present in an object. The method to detect manufacturing defects includes an algorithm for analyzing the pattern of geometric elements in an array and detecting deviations from numerical acceptance norms, such as diameter, spacing, and symmetry, for the geometric elements. In the inventive system, a one-dimensional video camera captures a single one-dimensional "slice" of target shape of an object with every line it scans. Each slice is broken down into "segments" consisting of sets of adjacent pixels that are similar in brightness, hue, or both. The one-dimensional camera, in conjunction with processing by ancillary electronic data processing means and methods, delivers the segments to the system where they are sequenced. The system identifies every segment to determine what feature of the target shape the segment represents. Thereafter, predefined rules are used to determine if each identified segment deviates from numerical acceptance norms. The inventive method is thus used to analyze periodic arrays of any arbitrary target shape, thereby working in a range of different object acceptance norms and being easily adaptable to change from one set of norms to another.

The algorithm used in the inventive method accomplishes at least two outcomes simultaneously. It serves as a framework, for the transformation of a set of measurements that could be made on a two-dimensional image of the target area into a set of measurements made only on the one-dimensional data set. In addition, the algorithm is capable of accurately measuring a lattice constant, i.e., the spacing between the geometric elements of an array that arises from a data set only after certain manipulations have been made.

The lattice constant can be measured without prior knowledge of any scan line other than the one currently being observed. Thus, it is never necessary to assemble a two-dimensional depiction of the one-dimensional video data, or of any product data arising from the manipulation of the video data. This is important in a design of computational hardware to analyze the video data stream generated by any camera, such as a one-dimensional camera or a two-dimensional camera.

Specifically, in a preferred embodiment, the algorithm is used to inspect aperture masks with arrays of annular elements The inventive method uses a pattern rule, derived from the geometry of the annular elements, and a lattice constant rule for estimating the spacing between annular elements of an array, whereby not all possibilities in the analysis work. It should be noted that other rules may be used in inspecting other objects with arrays of geometric elements. The one-dimensional video camera captures a single one-dimensional scan line of target shape of an object. First, the line scan data is reduced to a collection of numbers, each representing the brightness of a particular pixel, to "run-length encoded" data. In an embodiment of the invention, the system reduces the scan line data to black and white images by determining if the data is darker or brighter than a predefined threshold. Thus, each pixel in the image is reduced to a single bit in the system. As would be apparent to one of ordinary skill in the art, there are other ways of reducing the data to binary data. A consecutive set of all dark or white pixels in an annular element is thus defined as a run. In an alternate embodiment, the system works on data represented in non-binary formats. For example, the system will work with multi-color data encrypted by three or more bits or with analog data in a numeric form.

The system thereafter generates a set of run-length integers from the reduction of the scan line data. The algorithm implemented in the inventive method applies a technique of search to analyze run-length data derived from the line scan data. Using the pattern and lattice constant rules, systematic accounting of every possible interpretation of each of the run-length integers is made, whereby each interpretation is systematically tested and those interpretations that cannot be valid are ignored. When an interpretation is deemed to be invalid, any more extensive interpretation, of which this is only a part, is likewise invalid, and further processing power need not be expended to check it. Thus, the inventive method is used to detect manufacturing defects by detecting paths that deviate from numerical acceptance norms for the annular elements in an array.

A symbolic designation is assigned to each run. Symbolic designations under dark runs, in the aperture mask inspection, include a sliver (SLIV), an entry vertical (NV), and an exit vertical (XV) and symbolic designations under light runs include "LAND" and "HOLE". SLIV is the designation used when the scan line passes through the dark sections on the top or bottom of a ring. Entry vertical is the designation used when the scan line passes through the dark section on the right of the center of the hole. Exit vertical is the designation used when the scan line passes through the dark section on the left of the center of the hole. HOLE is the designation used when the scan line passes through the light center of the hole and LAND is the designation used when the scan line passes through the light section outside of the hole.

As would be apparent to those of ordinary skill in the art, rules used in the inventive method may be modified as long as there are enough defined rules to keep the systematic accounting of every possible interpretation from growing out of bounds and as long as the inspection problem is computable. That is, each path created from the systematic accounting of every possible interpretation in a scan line can be computed in the system, in parallel by multiple simple processors at very high speed.

It is therefore an object of the invention to provide a system and method for inspecting electronically acquired imagery, one-dimensional video cameras, by capturing a single one-dimensional "slice" of target shape with every line the camera scans. The method includes means for breaking down each slice into segments, identifying every segment to determine what feature of the target shape the segment represents, sequencing each segment and using rules, to determine if each identified segment deviates from numerical acceptance norms for an annular element.

It is another object of the invention to provide a method for transforming a set of measurements that could be made on a two-dimensional image of the target area into a set of measurements made only on the one-dimensional data set and for measuring the lattice constant.

It is another object of the invention to provide a method for using rules, such as the pattern rule and the lattice constant rule, whereby not all possibilities in the analysis work. The rules in the inventive method can be made to work even when the camera alignment is accidental.

It is another object of the invention to provide a system and method for producing integers from the reduction of the scan line data, whereby a collection of numbers each representing the brightness of a particular pixel, to "run-length encoded" data results in the integers.

It is another object of the invention to provide a technique or search method for systematically accounting for every possible interpretation of each of the run-length integers and ignoring those interpretations that cannot be valid.

It is yet another object of the invention to provide a computational system and method for analyzing every possible interpretation of each of the run-length integers in parallel.

Additional features and advantages of the invention will be set forth in the description that follows, and in part will be apparent from the description, or may be learned by practice of the invention. The objectives and advantages of the invention will be realized and attained by the system particularly pointed out in the written description and claims hereof as well as the appended drawings.

To achieve these and other advantages and in accordance with the purpose of the invention, as embodied and broadly described, the present invention provides a method in a system for using electronically acquired imagery from a one-dimensional camera to inspect an object for a wide variety of manufacturing defects, the method comprising the steps of: capturing, by the one-dimensional camera, a one-dimensional scan line of the electronically acquired imagery whereby each scan line includes an array of geometric elements; delivering the scan line to the system; sequencing the scan line, passing a horizontal line through the array of geometric elements, and reducing the scan line to a plurality of run-length integers whereby each run-length integer represents one run; systematically accounting for all possible interpretations of each run using a plurality of predefined rules to determine deviations from a set of acceptance norms for the array of geometric elements; and systematically testing each interpretation wherein invalid interpretations are ignored.

The invention also provides a system for using a one-dimensional camera to inspect electronically acquired imagery of an object for a wide variety of manufacturing defects, the system comprises: a one-dimensional camera for capturing a single one-dimensional scan line of the electronically acquired imagery whereby each scan line includes an array of geometric elements; means for delivering the scan line from the one-dimensional camera to a computer system; and software means in the computer system for processing and reducing the scan line to a plurality of run-length integers whereby each run-length integer represents one run, systematically accounting for all possible interpretations of each run using a plurality of predefined rules to determine deviations from a set of acceptance norms for the array of geometric elements, systematically testing each interpretation, and ignoring invalid interpretations.

The invention also provides a software component in a computer system for inspecting electronically acquired imagery of an object for a wide variety of manufacturing defects, the software component comprises: first processing mean for processing and reducing a scan line, with an array of geometric elements, to a plurality of run-length integers whereby each run-length integer represents one run; second processing means for systematically accounting for all possible interpretations of each run using a plurality of predefined rules to determine deviations from a set of acceptance norms for the array of geometric elements; third processing means for systematically testing each interpretation and for ignoring invalid interpretations.

The invention also provides a system for using a one-dimensional camera to inspect electronically acquired imagery of an object for a wide variety of manufacturing defects, the system comprises: a one-dimensional camera for capturing a one-dimensional scan line of the electronically acquired imagery whereby each scan line includes an array of geometric elements; means for delivering the scan line from the one-dimensional camera to a computer system; and software means in the computer system for processing and reducing the scan line to a plurality of run-length integers whereby each run-length integer represents one run, systematically accounting for all possible interpretations of each run using a plurality of predefined rules to determine deviations from a set of acceptance norms for the array of geometric elements, systematically testing each interpretation, and ignoring invalid interpretations; and a plurality of simple processors for parallel processing of a plurality of interpretations at very high speed.

BRIEF DESCRIPTION OF THE DRAWINGS

The accompanying drawings, which are included to provide a further understanding of the invention and are incorporated in and constitute a part of this specification, illustrate embodiments of the invention that together with the description serve to explain the principles of the invention.

In the drawings:

FIG. 1-A illustrates a two-dimensional image obtained from a two-dimensional camera, where the horizontal black line represents a one-dimensional "scan line;"

FIG. 1-B illustrates a row of annular elements, from FIG. 1-A, as shown in isolation;

FIG. 1-C illustrates a row of annular elements having vertical position adjustments;

FIG. 1-D illustrates a resulting composite image from FIG. 1-A;

DETAILED DESCRIPTION

Reference will now be made in detail to the preferred embodiments of the present invention, examples of which are illustrated in the accompanying drawings. The present invention described below extends the functionality of the inventive method for inspecting objects with arrays of annular rings.

In the invention, electronically acquired imagery of an object, from a one-dimensional video camera, is inspected for tolerance, color, blemishes, cracks or a wide variety of manufacturing defects that might be present. Equipment for one-dimensional video imaging is less expensive per unit of performance than is equipment for two-dimensional video imaging and it is easier to illuminate a line target than an area target. Moreover, one-dimensional data is collected over a much smaller time-scale than two-dimensional video data. This advantage is likely to increase over time since technical improvements in two-dimensional technology will be applicable to one-dimensional equipment. The system using a one-dimensional camera also detects every flaw detected by systems operating on two-dimensional data from conventional two-dimensional cameras.

Specifically in the invention, a one-dimensional video camera, such as a line scan camera, captures a single one-dimensional "slice" of target shape with every line it scans. Each slice is broken down into "segments" consisting of sets of adjacent pixels that are similar in brightness, hue, or both. An algorithm used in the inventive method identifies every segment to determine what feature of the target shape the segment represents. Rendering of the target shape into features may be accomplished using techniques for automatically resolving a physical object into finite elements for stress or thermal analysis. As segments are delivered into the system by the line scan camera, they are sequenced, and predefined rules are used to determine whether a particular identity assignment accurately reflects numerical acceptance norms. The inventive method is thus able to analyze periodic arrays of any arbitrary target shape, and the effectiveness of the system actually improves for more complex target shapes. As long as the rules used when implementing the method keep the number of choices from growing without bound, the system is able to locate at least one set of labels in which every segment has exactly one label, which "explains" the segment. In a preferred embodiment of the invention, the rules discover the inner and outer diameter, and spacing, of every hole in a scan line without any prior information about these parameters. If prior information is available, the computational system uses the prior information to complete the task more rapidly.

Figure 1:
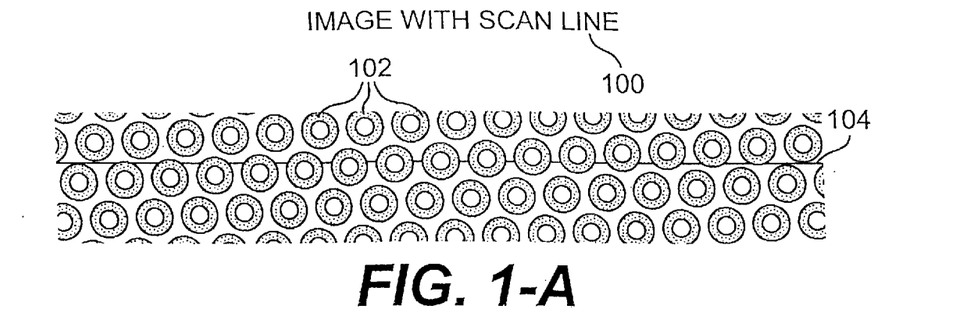

FIGS. 1-A to 1-D illustrate a progression of different depictions of the same data and they are used to illustrate how the algorithm in the inventive method functions. FIG. 1-A illustrates an image 100, which is a two-dimensional depiction of a region covered by an array of annular rings 102. Horizontal black line 104 is intended to show the locus of all points covered by a single scan line derived from a one-dimensional video camera that is positioned so as to observe the ring pattern. FIG. 1-B illustrates a scan line 106, from FIG. 1-A, as shown in isolation. Scan line 106 shows only those rings that are near, or in contact with horizontal black line 104. Since the rings that are not proximate to horizontal line 104 cannot be seen by the one-dimensional camera, they do not contribute any data to scan line 106.

Thus, nothing is changed when they are omitted from the picture. FIG. 1-C illustrates scan line 108, from FIG. 1-B, which is adjusted. Specifically, the rings in adjusted scan line 108 are displaced vertically in order to bring them into horizontal alignment. As each ring is displaced, the segment of the scan line that is in the neighborhood of the ring is also moved in order that the data produced by the scan line not be altered. The act of "breaking" up the scan line between FIG. 1-B and FIG. 1-C implies that "break points" or lattice constants, are placed along the length of the line. The lattice constants are spacing between annular elements 102 of the array that arises from the data set only after certain manipulations have been made. By knowing the element spacing, the two-dimensional analysis problem can be transformed into a one-dimensional analysis problem, at least for arrays of identical objects.

FIG. 1-D illustrates a resulting composite 110 image from FIG. 1-A, whereby the dark and light segments arising from the scan line are stacked vertically. By so doing, a composite image of what appears to be a single annulus is created. Composite image 110 is created from data taken from the collection of all seventeen annuli 102 that are seen by the camera. The two-dimensional "composite" representation 110 of the data is the result of the angular displacement between the axis of the scan line and the major axis of symmetry of the array pattern. This displacement gives rise to a scanning phenomenon that enables the system to re-create an apparently two-dimensional image of a single annulus. If the scan line is perfectly aligned with one or another symmetry axis of the array, the scanning behavior will not be seen. Thus, there are certain forbidden/accidental orientations of the line-scan camera at which an algorithm implemented in the inventive method will not work as well. In practice the range of forbidden orientations is small when compared to the total number of possible orientations and alignments that can occur between a physical camera and a physical annulus array. Nevertheless, the analytical technique implemented in the inventive method can be made to work even when the camera alignment is "accidental;" however, a different set of measurement parameters must be brought to play. In most cases, these accidental situations can be "detected" by the method for inspecting the image.

Any set of measurements, or rules describing measurements, that can be made on the individual annular elements 102 can be made just as well on the composite image 110. What is needed is a means, or method, by which those measurements and rules can be transformed into an algorithm that takes as its input the data in pixel form. The data that arises from a two-dimensional depiction of the pattern is all present in the one-dimensional data set.

Figure 2:
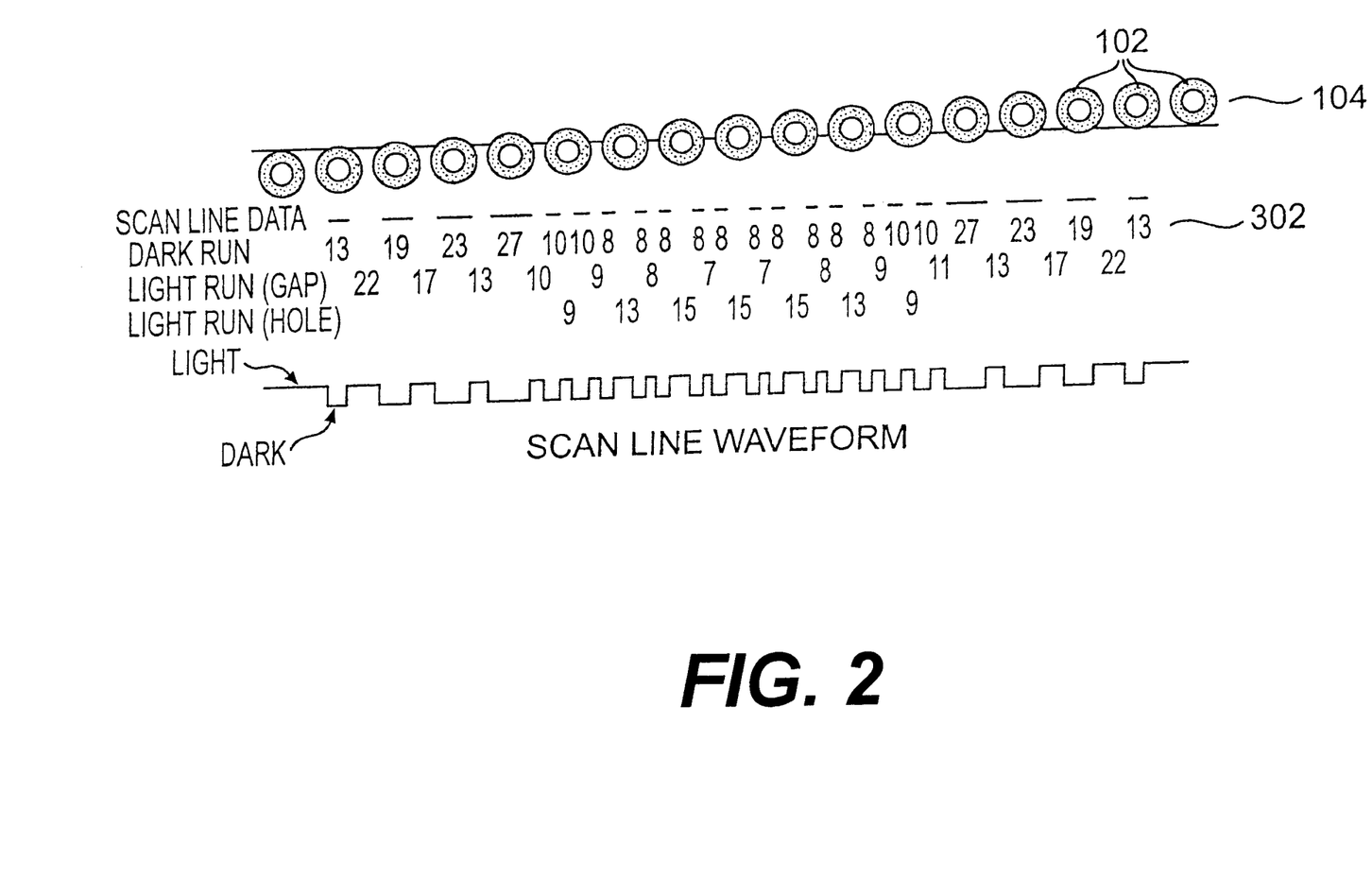
FIG. 2 illustrates a set of integers that results from the reduction of the scan line data.
Figure 3:
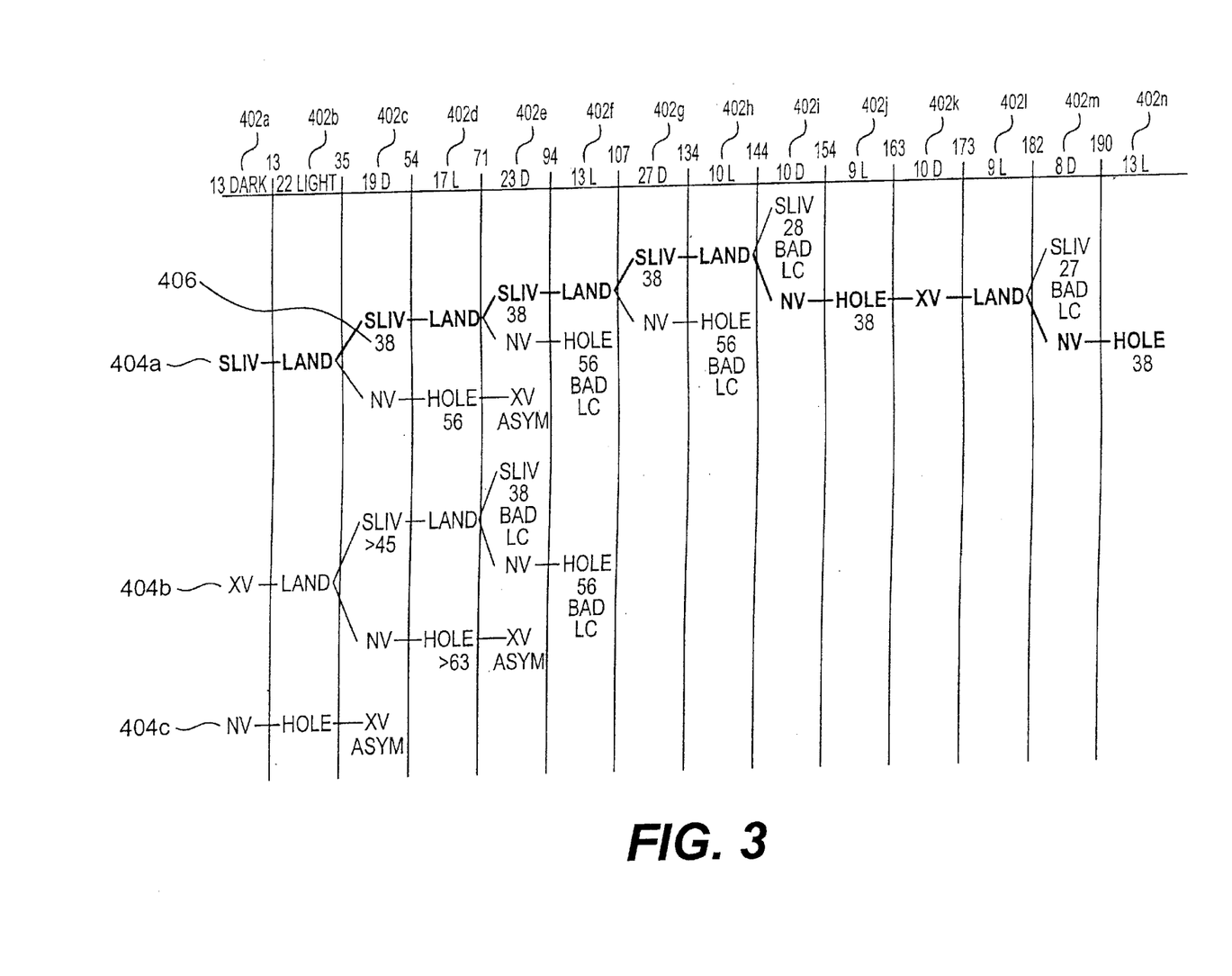
FIG. 3 illustrates the operation of the algorithm in the inventive method.
Figure 4:
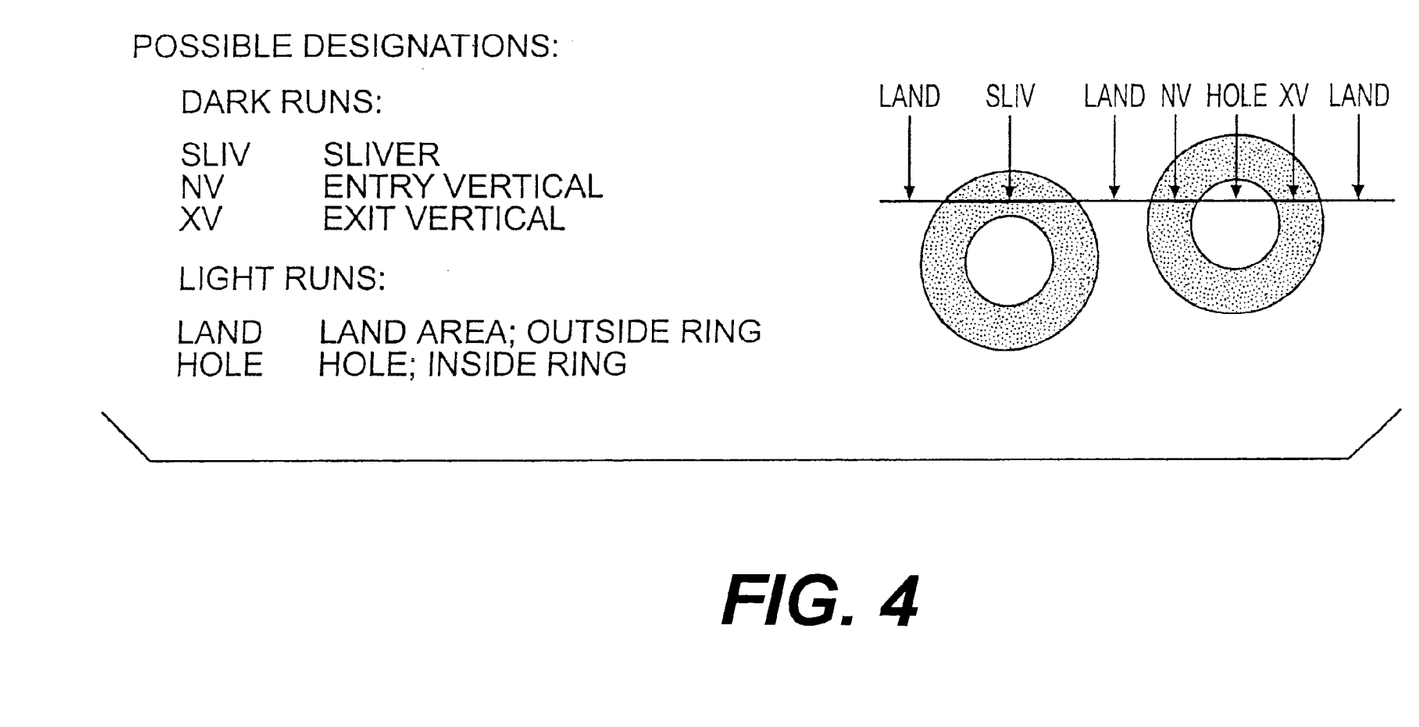
FIG. 4 illustrates symbolic designations under columns in FIG. 3.

FIGS. 2 to 4 illustrate how the algorithm in the inventive method is implemented on a scan line from a one-dimensional camera. The algorithm is essentially an application of a technique of search during analysis of run-length data that is derived from the scan line.

FIG. 2 illustrates a set of integers 202 that results from the reduction of the scan line data. Integers 202 result from a collection of numbers each representing the brightness of a particular pixel, to "run-length encoded" data. The system reduces the scan line data to black and white images by determining if the data is darker or brighter than a predefined threshold. Thus, each pixel is reduced to a single bit in the computer. A consecutive set of all dark or white pixels in annular element/ring 102 through which horizontal line 104 passes is defined as a run. In FIG. 2 horizontal line 104 misses the first hole entirely so there is no run for this hole. The first run is a dark run with a length of 13, since horizontal line 104 passes through the dark section on top of the second hole. The next run is a light run with a length of 22, representing where horizontal line 104 passes through the gap between the second and third holes. Integers 202 representing each run are taken off a computer screen after the system reduces the scan line data from the line scan camera. It is these integers 202, i.e., 13, 22, 19, 17 . . . reading from left to right in FIG. 2, that are submitted as input to the algorithm in the inventive search method.

FIG. 3 illustrates a search tree for the first fourteen runs of the data in FIG. 2. In FIG. 3, a systematic accounting of every possible interpretation of each of the run-length integers 202 is made. Thus, columns 302a–302n each correspond to one run, whereby at the top of each column 302a–302n is the length of the run and a word or letter designating the run's illumination state as either "light", "L" or "dark", "D." For example, the first column's 302a heading is "13 Dark," because the first complete run shown in FIG. 2 is a dark run of length 13.

FIG. 4 illustrates symbolic designations for each run. In an embodiment of the invention, symbolic designations under dark runs include a sliver (SLIV), an entry vertical (NV), and an exit vertical (XV). Symbolic designations under light runs include "LAND" and "HOLE". SLIV is the designation used when horizontal line 104 passes through the dark sections on the top or bottom of ring 102. Entry vertical is the designation used when horizontal line 104 passes through the dark section on the left of the center of ring 102. Exit vertical is the designation used when horizontal line 104 passes through the dark section on the right of the center of ring 102. HOLE is the designation used when horizontal line 104 passes through the light center of ring 102, and LAND is the designation used when horizontal line 104 passes through the light section outside of ring 102.

Referring back to FIG. 3, rows 304a–c represent possible interpretations of each run. For example, since the first run is a dark run, horizontal line 104 can only pass over the top or bottom sections (a SLIV run), the dark section on the left of the center (a NV run), or the dark section on the right of the center (a XV run). Thus, based on designations in the left column of each row, rows in FIG. 3 are used to create paths that account for every possible interpretation of each run. Upon interpreting each of run length integers 202, the "correct" path 304a, that is, the path that corresponds to the correct interpretation of the run-length data, is shown in bold print with heavy lines. The search technique implemented by the inventive algorithm is a systematic way of testing each interpretation and ignoring those interpretations that cannot be valid. When an interpretation is deemed to be invalid, any more extensive interpretation, of which this is only a part, is likewise invalid, and further processing power need not be expended to check it.

In FIG. 3, the annotations under some of the symbolic designations, particularly those that terminate a search path, show information that is discovered by interpreting the larger pattern of runs. For example, as soon as any path contains two SLIV runs, the lattice constant parameter may be estimated using a lattice constant rule. The lattice constant rule estimates the distance between previous runs. First a center point of the first SLIV or HOLE run is calculated by dividing the length of the run by two and rounding the decimal number to the next integer. By interpreting one path at a time, the rule adds the length of the first SLIV or HOLE run to the length of next run. The center point of the next SLIV or HOLE run is estimated by dividing the length of the run by 2, rounding up to the next integer and adding the quotient to the cumulative length. The center of the first SLIV or HOLE run, subtracted from the center of the second SLIV or HOLE run, equals the center-to-center distance, i.e., the distance between the first SLIV or HOLE run and the second SLIV or HOLE run. If there is discrepancy in the spacing between two SLIV and/or HOLE runs, analysis of the path is terminated under the lattice constant rule. This is because the center point of a SLIV or HOLE run must be at or close to the centerline of the annulus to which the SLIV or HOLE run belongs. Using the lattice constant rule, when a path has more than two HOLE or SLIV runs, more than one estimate of lattice constants can be made. If the estimated lattice constants are inconsistent with each other, that path contains an erroneous labeling and further interpretation of the path is terminated.

As shown in FIG. 3, the inventive system implementing the inventive method does not use brute force in analyzing each run, but instead uses a pattern rule based on the geometry of the targets and the lattice constant rule, whereby not all possibilities in the analysis work. An example of brute force analysis is testing all possibilities of a run by making determinations, such as if a SLIV run is the first run, the next run has to be a LAND run and so on. The inventive method eliminates such brute force by terminating interpretations of paths rendered invalid by appropriate rules. In an embodiment of the invention, the method uses a symmetry rule for a circle. To illustrate how the circle rule is implemented, note at the bottom of column 302a, the method assumes that the run is a NV run. Thus, the next run must be a HOLE run and the following run must be an XV run. Upon analyzing the path, the entry vertical length is 13 and the exit vertical length is 19. Since the geometry of the hole is a circle, this path fails for asymmetry.

Using the lattice constant rule, for example in FIG. 3 path 304a, the method estimates the distance between previous runs. The SLIV run in column 302a, a dark run of length 13, has a center point of 6.5 which is thirteen divided by two. All decimal numbers in this rule are rounded to the next integer and so the center point of the first SLIV run is 7. The next run must be a LAND run, and analyzing along one path at a time, the following runs must be a SLIV run or an NV run. In FIG. 3, the numbers above the vertical lines represent a cumulative position. The number above the second vertical line, 35, represents the addition of the 13, the length of the first SLIV run, and 22, length of the light run in column 302b. The second SLIV run in that path has the center 45, which is the total of the quotient of 19, (the length of the dark run in column 302c, divided by 2 and rounded to the next integer) and added to 35 (the cumulative number from the top of the second vertical line). The center of the first SLIV run, 7, subtracted from the center of the second SLIV run, 45, equals to the center-to-center distance 306. In FIG. 3, center-to-center distance 306 is the number represented under the second SLIV run, which in this case is 38. The next run in this path is a LAND run followed by a SLIV run and a NV run. Analyzing one path at a time, the run following the NV run has to be a HOLE run. The center of the HOLE is 101, i.e., the 13, the length of the run, divided by 2 and rounded up to the next integer plus 94 which is the cumulative length up to that HOLE. Using the lattice constant rule, a spacing calculation between the second SLIV run and the first HOLE run in this path shows a discrepancy. The spacing is 56, which is the center-to-center distance between the second SLIV and the HOLE. With the first spacing between the first and second SLIV runs estimated at 38, a spacing of 56 between the second SLIV run and the HOLE run does not correspond with the first spacing. Another spacing of 38 or a close number would be more acceptable. Thus, the lattice constant rule eliminates this path.

By using the pattern rule and the lattice constant rule, the algorithm can be used to analyze the pattern of rings in an array and to detect deviations from numerical acceptance norms, such as ring diameter, spacing, and symmetry for annular targets. Thus, the algorithm may be used to inspect a manufactured object where inspection of an array of annular ring for a defect is required.

As would be apparent to those of ordinary skill in the art, rules used in the inventive method may be modified as long as there are enough defined rules to keep the sorting tree from growing without bound. This makes the inspection problem computable, that is, paths can be computed in parallel by multiple simple processors at very high speed. Using relatively cheap chips that can be programmed with AND gates and OR gates, a system implementing the inventive method can easily perform 100 billion operations per seconds. Thus, the method is expressible as a custom or semi-custom integrated circuit chip and can scale well to a highly parallel implementation. Moreover the path-analysis method works even in the presence of considerable noise and other real-world imperfections. The inventive algorithm can be extended for use with slot-shaped holes, which appear as oval targets in the video image. The algorithm has shown the capacity to distinguish automatically between circular and slot-shaped holes.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A method in a system for using electronically acquired imagery from a one-dimensional camera to inspect an object for a wide variety of manufacturing defects, the method comprising the steps of:

capturing, by the one-dimensional camera, a one-dimensional scan line of the electronically acquired imagery whereby each scan line includes an array of geometric elements;

delivering the scan line to the system;

sequencing the scan line, passing a horizontal line through the array of geometric elements, and reducing the scan line to a plurality of run-length integers whereby each run-length integer represents one run;

systematically accounting for all possible interpretations of each run using a plurality of predefined rules to determine deviations from a set of acceptance norms for the array of geometric elements; and systematically testing each interpretation wherein invalid interpretations are ignored.

2. The method of claim 1, wherein each geometric element in the array has a same geometric shape.

3. The method of claim 2, wherein the array of geometric elements is an array of annular elements.

4. The method of claim 3, wherein the step of systematically accounting further comprises the step of assigning a symbolic designation to each run of the annular element.

5. The method of claim 4, wherein the step of assigning a symbolic designation further comprises the steps of:

designating a dark run as a sliver run when the horizontal line passes through dark sections on a top or bottom of the annular element in the array of geometric elements;

designating the dark run as an entry vertical run when the horizontal line passes through dark sections on a left of a center of the annular element in the array of geometric elements;

designating the dark run as an exit vertical run when the horizontal line passes through dark sections on a right of the center of the annular element in the array of geometric elements;

designating a light run as a HOLE run when the horizontal line passes through a light center of the annular element in the array of geometric elements; and designating the light run as a LAND run when the horizontal line passes through a light section between two annular elements in the array of geometric elements.

6. The method of claim 5, wherein the step of systematically accounting further comprises the step of applying each run to a search tree table having rows and columns and systematically accounting for every possible interpretation of each of the plurality of run-length integers.

7. The method of claim 6, wherein each interpretation is an interpretation path in the search tree table.

8. The method of claim 7, wherein the step of systematically accounting further comprises the step of corresponding each run to a column in the search tree table, whereby a top of each column shows a length of the run and a word or letter designating an illumination state of the run as either light or dark.

9. The method of claim 8, wherein the step of systematically accounting further comprises the step of corresponding each interpretation of a run to a row in the search tree table.

10. The method of claim 9, wherein the step of corresponding each interpretation further comprises the step of basing designations of a current column, in the interpretation path, on designation in a previous column in the same interpretation path.

11. The method of claim 10, wherein as soon as the interpretation path contains two sliver runs, a lattice constant parameter may be estimated using a lattice constant rule whereby the lattice constant rule is used estimate the distance between previous runs in the interpretation path.

12. The method of claim 11, wherein as soon as the interpretation path contains two hole runs, a lattice constant parameter may be estimated using the lattice constant rule whereby the lattice constant rule is used estimate the distance between previous runs in the interpretation path.

13. The method of claim 11 or 12, wherein the step for estimating the lattice constant parameter comprises the steps of:

calculating a first center point of the first sliver or hole run by dividing the length of the first sliver or hole run by two and rounding to a next integer;

adding the length of the first sliver or hole run to the length of the next run in an interpretation path;

calculating a second center point of a next sliver or hole run by dividing the length of the second sliver or hole run by two, rounding to a second integer and adding the second integer to the length of a cumulative length of all preceding runs in a path;

subtracting the first center point from the second center point;

determining if there is discrepancy in spacing between two sliver or two hole runs and terminating the interpretation path if there is discrepancy.

14. The method of claim 1, wherein the step of delivering is performed by the one-dimensional camera in conjunction with other ancillary electronic data processing means and methods.

15. The method of claim 1, wherein the step of reducing further comprises the step of defining a run as a consecutive set of all dark or light pixels in the array of geometric elements through which the horizontal line passes.

16. The method of claim 15, wherein the step of reducing further comprises the step of creating a collection of numbers, each representing a brightness of a particular pixel in a run-length encoded data.

17. The method of claim 16, wherein the step of reducing further comprises the steps of:

breaking down the scan line into segments, whereby each segment comprises sets of adjacent pixels that are similar in brightness or hue or similar in brightness and hue; and representing each segment with one of the plurality of run-length integers.

18. The method of claim 17, wherein the step of reducing further comprises the step of identifying every segment to determine what features of the object the segment represents.

19. The method of claim 18, wherein the step of identifying every segment comprises the step of locating at least one set of labels in which every segment in the scan line has at least one label that defines the segment.

20. The method of claim 19, wherein the step of reducing further comprises the step of reducing data in the scan line to black and white images by determining if the data is darker or brighter than a predefined threshold and reducing each pixel to a single bit in the system.

21. The method of claim 19 or 20, wherein the step of reducing further comprises the step of defining a run as a light run if the horizontal line passes through a light part of the geometric element.

22. The method of claim 21, wherein the step of reducing further comprises the step of defining a run as a dark run if the horizontal line passes through a dark part of the geometric element.

23. The method of claim 19, wherein the step of reducing further comprises the step of reducing data in the scan line to non-binary format whereby the data is reduced to multiple bits.

24. The method of claim 1, wherein one of the predefined rules is a lattice constant rule for measuring spacing between the geometric elements in the array of geometric elements whereby a lattice constant is be measured without prior knowledge of the scan line being observed.

25. The method of claim 1, wherein one of the predefined rules is a pattern rule that is derived from a geometry of the geometric elements.

26. A system for using a one-dimensional camera to inspect electronically acquired imagery of an object for a wide variety of manufacturing defects, the system comprises:

a one-dimensional camera for capturing a one-dimensional scan line of the electronically acquired imagery whereby each scan line includes an array of geometric elements;

means for delivering the scan line from the one-dimensional camera to a computer system; and software means in the computer system for processing and reducing the scan line to a plurality of run-length integers whereby each run-length integer represents one run, systematically accounting for all possible interpretations of each run using a plurality of predefined rules to determine deviations from a set of acceptance norms for the array of geometric elements, systematically testing each interpretation, and ignoring invalid interpretations.

27. The system of claim 26, wherein each geometric element in the array has a same geometric shape.

28. The system of claim 26, wherein the array of geometric elements is an array of annular elements.

29. The system of claim 26, wherein means for delivering the scan line is performed in the one-dimensional camera in conjunction with other ancillary electronic data processing means.

30. The system of claim 26, wherein the software means:

defines a run as a consecutive set of all dark or light pixels in the array of geometric element through which a horizontal line passes;

creates a collection of numbers each representing a brightness of a particular pixel in a run-length encoded data;

breaks down the scan line into segments, whereby each segment comprises sets of adjacent pixels that are similar in brightness or hue or similar in brightness and hue;

represents each segment with one of the plurality of run-length integers; and identifies every segment by locating at least one set of labels in which every segment in the scan line has at least one label that defines the segment.

31. The system of claim 30, wherein the software means:

reduces data in a scan line to black and white images by determining if the data is darker or brighter than a predefined threshold and reducing each pixel to a single bit in the system; or reduces data in a scan line to non-binary format whereby the data is reduced to multiple bits.

32. The system of claim 31, wherein the software means:

defines the run as a light run if the horizontal line passes through a light part of the geometric element; and defines the run as a dark run if the horizontal line passes through a dark part of the geometric element.

33. The system of claim 26, wherein the predefined rules comprises:

a lattice constant rule for measuring spacing between the geometric elements in the array, whereby a lattice constant is be measured without prior knowledge of the scan line being observed; and a pattern rule that is derived from a geometry of the geometric elements.

34. The system of claim 26, wherein the software means assigns a symbolic designation to each run by:

designating a dark run as a sliver run when the horizontal line passes through dark sections on a top or bottom of an annular element in the array of geometric elements;

designating the dark run as an entry vertical run when the horizontal line passes through dark sections on the left of a center of the annular element;

designating the dark run as an exit vertical run when the horizontal line passes through dark sections on a right of the center of the annular element;

designating a light run as a HOLE run when the horizontal line passes through a light center of the annular element; and designating the light run as a LAND run when the horizontal line passes through a light section between two annular elements.

35. The system of claim 34, wherein the software means applies each run to a search tree table having rows and columns and systematically accounts for every possible interpretation of each of the plurality of run-length integers by creating an interpretation path in the search tree table for each interpretation.

36. The system of claim 35, wherein the software means corresponds each run to a column in the search tree table, whereby a top of each column shows a length of the run and a word or letter designating illumination state of the run as either light or dark; and corresponds each interpretation of a run to a row in the table, and bases designations of a current column, in an interpretation path, on designation of a previous column in the same interpretation path.

37. The system of claim 36, wherein as soon as the interpretation path contains two sliver runs, a lattice constant parameter is estimated using a lattice constant rule whereby the lattice constant rule is used to estimate the distance between previous runs in the path, the lattice constant parameter is estimated by calculating a first center point of a first sliver or hole run by dividing the length of the first sliver or hole run by two and rounding to a first integer;

adding the length of the first sliver or hole run to the length of the next run in an interpretation path;

calculating a second center point of a second sliver or hole run by dividing the length of the second sliver or hole run by two, rounding to a second integer and adding the second integer to the length of a cumulative length of all preceding runs in a path;

subtracting the first center point from the second center point;

determining if there is discrepancy in spacing between two sliver or two hole runs and terminating the interpretation if there is discrepancy.

38. A software component in a computer system for inspecting electronically acquired imagery of an object for a wide variety of manufacturing defects, the software component comprises:

first processing mean for processing and reducing a scan line, with an array of geometric elements, to a plurality of run-length integers whereby each run-length integer represents one run;

second processing means for systematically accounting for all possible interpretations of each run using a plurality of predefined rules to determine deviations from a set of acceptance norms for the array of geometric elements;

third processing means for systematically testing each interpretation and for ignoring invalid interpretations.

39. The software component of claim 38, wherein the first processing means:

defines a run as a consecutive set of all dark or light pixels in the array of geometric element through which a horizontal line passes;

creates a collection of numbers each representing the brightness of a particular pixel in a run-length encoded data;

breaks down the scan line into segments, whereby each segment comprises sets of adjacent pixels that are similar in brightness or hue or similar in brightness and hue;

represents each segment with one of the plurality of run-length integers; and identifies every segment by locating at least one set of labels in which every segment in the scan line has at least one label that defines the segment.

40. The software component of claim 39, wherein the first processing means:
  reduces data in a scan line to black and white images by determining if the data is darker or brighter than a predefined threshold and reducing each pixel to a single bit in the system; or
  reduces data in the scan line to non-binary format whereby the data is reduced to multiple bits.

41. The software component of claim 40, wherein the first processing means:
  defines the run as a light run if the horizontal line passes through a light part of the geometric element in the array of geometric elements; and
  defines the run as a dark run if the horizontal line passes through a dark part of the geometric element in the array of geometric elements.

42. The software component of claim 38, wherein the predefined rules comprises:
  a lattice constant rule for measuring spacing between the geometric elements in the array, whereby a constant can be measured without prior knowledge of the scan line being observed; and
  a pattern rule that is derived from the geometry of the geometric elements.

43. The software component of claim 38, wherein the second processing means assigns a symbolic designation to each run by:
  designating a dark run as a sliver run when the horizontal line passes through dark sections on a top or bottom of an annular element in the array of geometric elements;
  designating the dark run as a entry vertical run when the horizontal line passes through dark sections on a left of a center of the annular element in the array of geometric elements;
  designating the dark run as an exit vertical run when the horizontal line passes through dark sections on a right of the center of the annular element in the array of geometric elements;
  designating a light run as a HOLE run when the horizontal line passes through a light center of the annular element in the array of geometric elements; and
  designating the light run as a LAND run when the horizontal line passes through a light section between two annular elements in the array of geometric elements.

44. The software component of claim 38, wherein the third processing means applies each run to a search tree table having rows and columns and systematically accounts for every possible interpretation of each of the plurality of run-length integers by creating an interpretation path in the search tree table for each interpretation.

45. The software component of claim 44, wherein the third processing means corresponds each run to a column in the search tree table, whereby the top of each column shows a length of the run and a word or letter designating an illumination state of the run as either light or dark;
  corresponds each interpretation of a run to a row in the table; and
  bases designations for a current column, in the interpretation path, on designation in a previous column in the same interpretation path.

46. The software component of claim 45, wherein as soon as the interpretation path contains two sliver runs, a lattice constant parameter is estimated using a lattice constant rule whereby the lattice constant rule is used to estimate the distance between previous runs in the path, the lattice constant parameter is estimated by
  calculating a first center point of a first sliver or hole run by dividing the length of the first sliver or hole run by two and rounding to a first integer;
  adding the length of the first sliver or hole run to the length of the next run in the interpretation path;
  calculating a second center point of a second sliver or hole run by dividing the length of the second sliver or hole run by two, rounding to a second integer and adding the second integer to a cumulative length of all preceding runs in a path;
  subtracting the first center point from the second center point;
  determining if there is discrepancy in the spacing between two sliver or two hole runs and terminating the interpretation if there is discrepancy.

47. A system for using a one-dimensional camera to inspect electronically acquired imagery of an object for a wide variety of manufacturing defects, the system comprises:
  a one-dimensional camera for capturing a one-dimensional scan line of the electronically acquired imagery whereby each scan line includes an array of geometric elements;
  means for delivering the scan line from the one-dimensional camera to a computer system; and
  software means in the computer system for processing and reducing the scan line to a plurality of run-length integers whereby each run-length integer represents one run, systematically accounting for all possible interpretations of each run using a plurality of predefined rules to determine deviations from a set of acceptance norms for the array of geometric elements, systematically testing each interpretation, and ignoring invalid interpretations; and
  a plurality of simple processors for parallel processing of a plurality of interpretations at very high speed.

* * * * *